United States Patent [19]
Maegawa et al.

[11] Patent Number: 5,711,272
[45] Date of Patent: Jan. 27, 1998

[54] FUEL PROPERTY DETECTION FOR AN ENGINE USING ENGINE SPEED

[75] Inventors: Yoshinori Maegawa; Hisashi Iida, both of Kariya, Japan

[73] Assignee: Denso Corporation, Kariya, Japan

[21] Appl. No.: 756,490

[22] Filed: Nov. 26, 1996

[30] Foreign Application Priority Data

Dec. 6, 1995 [JP] Japan ..................... 7-317851

[51] Int. Cl.⁶ ..................... F02P 5/15; G01N 33/22
[52] U.S. Cl. ..................... 123/418; 123/1 A; 73/116
[58] Field of Search ..................... 123/418, 1 A; 73/116, 117.3

[56] References Cited

U.S. PATENT DOCUMENTS 4,942,848  7/1990  Terasaka ..................... 123/1 A
5,419,296  5/1995  Yamaura ..................... 73/116
5,615,660  4/1997  Iwano et al. ..................... 123/680

FOREIGN PATENT DOCUMENTS 3-61644    3/1991  Japan .
3-233151  10/1991  Japan .

OTHER PUBLICATIONS

Patent Abstracts of Japan, vol. 16, No. 523, (M1331), Oct. 27, 1992, for JP 4-194348 (Sakata et al), Jul. 14, 1992.

*Primary Examiner*—Andrew M. Dolinar
*Attorney, Agent, or Firm*—Nixon & Vanderhye P.C.

[57] ABSTRACT

A fuel property, i.e., ordinary fuel, heavy fuel or mixture of both, is determined using an engine rotations. After an engine temperature exceeds 0° C. and an engine attains a complete combustion, an engine speed is integrated. It is determined whether a deviation between the integrated value of the engine speed and an integrated value of a set engine speed is larger than a predetermined determination value. As a result, it can be determined whether the fuel fed to the internal combustion engine has a volatility identical to that of the ordinary fuel, so that the fuel properties can be highly accurately determined.

12 Claims, 13 Drawing Sheets

FUEL PROPERTY DETECTION FOR AN ENGINE USING ENGINE SPEED

BACKGROUND OF THE INVENTION

1. Field of the Invention

The present invention relates to a fuel property detection for detecting the properties of a fuel fed to an internal combustion engine.

2. Description of Related Art

Fuel property detecting system for an internal combustion engine is disclosed in Japanese Patent Laid-Open Nos. 3-61644(1991) and 3-233151(1991). According to these prior art, the actual rotation speed (RPM) of the internal combustion engine and a preset threshold value are compared so that the volatility of a fuel fed to the internal combustion engine is determined from the fact that the engine RPM becomes lower than the threshold value.

This volatility determination is possible when the fuel fed to the internal combustion engine has an apparently poorer volatility (as will be simply called the "heavy fuel") than that of the ordinary fuel because such fuel of poor volatility will cause drop in the engine RPM in the end. For the mixed fuel which is prepared by mixing the ordinary fuel and the heavy fuel, however, the engine RPM drops so little that it makes it difficult to set the threshold value appropriately. Thus, it has been difficult to detect the ordinary fuel and the mixed fuel accurately.

SUMMARY OF THE INVENTION

The present invention therefore has an object to provide a fuel property detecting method and system for an internal combustion engine, which can determine the properties of a fuel fed to the internal combustion engine highly accurately even if the fuel is not only a heavy one but also a mixed one.

According to the fuel property detection of the present invention, an engine RPM, as detected for an elapsed time after the start, is integrated so that the volatility of the fuel fed to the internal combustion engine is determined on the basis of the integrated value of the engine RPM. As a result, it is possible to determine highly accurately whether the fed fuel of the internal combustion engine is an ordinary fuel having an excellent volatility or other heavy fuel (including a mixed fuel) having a poor volatility.

Preferably, the volatility of the fuel fed to the internal combustion engine is determined, after the engine RPM grows stable, on the basis of the result of comparing a deviation between the integrated value of the engine RPM at every predetermined timings and the integrated value of the set engine RPM, with a predetermined determination value or an offset value.

Preferably, the volatility of the fuel fed to the internal combustion engine is determined, after the engine RPM grows stable, on the basis of the result of comparing integrated value of the deviation between the engine RPM at every predetermined timings and the set engine RPM, with a predetermined determination value or an offset value.

Preferably, the determination is made before the internal combustion engine is completely warmed up and within a predetermined elapsed time range from the starting point. This is because the difference in the engine RPM due to the properties of the fed fuel is the less likely to appear as the internal combustion engine is the more warmed up or when the internal combustion engine is warmed after the predetermined elapsed time range from the starting point.

Preferably, no fuel enrichment (increase in fuel amount) is made if the air/fuel ratio of the exhaust gas from the internal combustion engine is at the rich side. As a result, it is possible to prevent the stall of the internal combustion engine, as might otherwise be caused by the excessive fuel enrichment to compensate for the heavy fuel.

Preferably, the angular delay of the ignition timing of the internal combustion engine is inhibited if it is determined that the fuel fed to the internal combustion engine is heavy and has a poor volatility. As a result the RPM of the internal combustion engine can be prevented in advance from becoming unstable, thereby to prevent the engine stall.

More preferably, the engine RPM, as detected for the elapsed time after the start when the cooling water temperature of the internal combustion engine exceeds a predetermined level, is integrated so that the volatility of the fed fuel to the internal combustion engine is determined on the basis of the integrated value of the engine RPM. As a result, the fuel property determination is not made when the cooling water temperature of the internal combustion engine is lower than the predetermined level so that the fuel enrichment is made. Thus, it is possible to determine highly accurately whether the fed fuel of the internal combustion engine is the highly volatile ordinary fuel or other heavy fuel (including the mixed fuel) having a poor volatility.

BRIEF DESCRIPTION OF THE DRAWINGS

Other objects, features and advantages of the present invention will be made more apparent by the following detailed description with reference to the accompanying drawings, in which.

DETAILED DESCRIPTION OF PRESENTLY PREFERRED EMBODIMENTS

The present invention will be described in further detail in connection with its embodiments with reference to the accompanying drawings.

<Embodiment 1>

Figure 1:
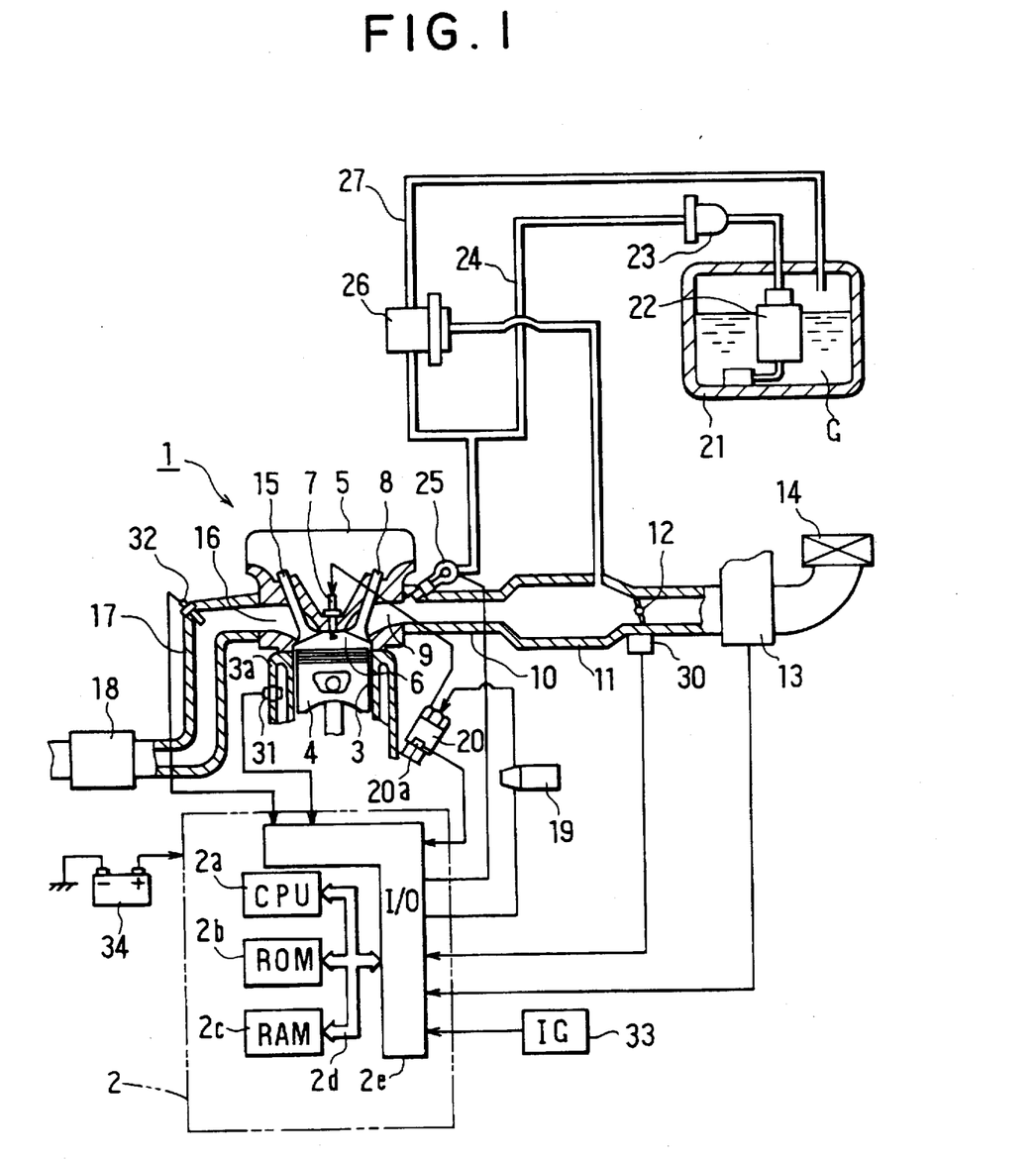
FIG. 1 is a schematic diagram showing a construction of a fuel property detecting system for an internal combustion engine according to a first embodiment of the present invention.

In FIG. 1 showing the first embodiment, reference numeral 1 designates an internal combustion engine, and numeral 2 designates an ECU (Electronic Control Unit). A cylinder 3, a piston 4 and a cylinder head 5 define a combustion chamber 6 of the internal combustion engine 1. An ignition plug 7 is mounted in the combustion chamber 6.

The intake system of the internal combustion engine 1 is constructed to include: an intake port 9 communicating with the combustion chamber 6 through an intake valve 8; an intake pipe 10 having a surge tank 11 for absorbing the pulsations of the intake air; a throttle valve 12 for adjusting the intake air flow amount; an air flow meter 13 for detecting the intake air flow amount; and an air cleaner 14.

On the other hand, the exhaust system of the internal combustion engine 1 is constructed to include: an exhaust port 16 communicating with the combustion chamber 6 through an exhaust valve 15; an exhaust pipe 17; and a catalyst converter 18 for purifying the exhaust gas.

Moreover, the ignition system of the internal combustion engine 1 is constructed to include: an igniter 19 for outputting a high voltage necessary for the ignition; a distributor 20 associated with the not-shown engine camshaft for distributing the high voltage, as generated by the igniter 19, to the ignition plug 7; and a rotation angle sensor 20a mounted in the distributor 20 for engine rotation speed detection.

Moreover, the fuel feed system of the internal combustion engine 1 is constructed to include: a fuel tank 21 for storing a fuel or gasoline G; a fuel pump 22 for pumping the gasoline G; a fuel filter 23 for filtering out foreign matters in the gasoline G; an injector (or electromagnetic fuel injection valve) 25 for injecting the gasoline, as pumped through a fuel pipe 24, into the intake port 9; and a pressure regulator 26 for regulating the fuel pressure to a predetermined level with respect to the intake pipe pressure. The excess amount of the gasoline G to be pumped is returned from the pressure regulator 26 through a return pipe 27 to the fuel tank 21.

The fuel property detecting system of the internal combustion engine is equipped as detectors with, in addition to the above-referred sensors and switches: a throttle position sensor 30 associated with the throttle valve 12 for detecting the throttle opening; a water temperature sensor 31 arranged in the cooling system of a cylinder block 3a for detecting the cooling water temperature of the internal combustion engine 1; and an oxygen sensor 32 arranged in the exhaust pipe 17 for detecting the concentration of the oxygen ($O_2$) residing in the exhaust gas.

The output signals of those sensors and switches are inputted to the ECU 2, which controls the injector 25 and the ignition plug 7 in the internal combustion engine 1 on the basis of the signals inputted thereto. To the ECU 2, moreover, there are inputted an on/off signal of an ignition switch (IG) 33 and the voltage of a battery 34.

The ECU is constructed by an arithmetic logic circuit composed mainly of: a CPU (central processing unit) 2a; a ROM 2b for storing a control program; and a RAM 2c for storing various data. The CPU 2a, ROM 2b and RAM 2c are connected to each other through a common bus 2d together with an input/output circuit (I/O) 2e which exchange inputs/outputs with the outside sensors and actuators.

For detecting the fuel properties, the CPU 2a of ECU 2 operates as follows based on the computer program shown in FIG. 2 and stored in the ROM 2b. This fuel property detecting routine is executed in the present embodiment at every 180 degrees CA (crank Angle) but may be at every other angular period (e.g., 30 degrees CA) or for each time period (e.g., 10 ms).

At first step S101 after engine starting, the engine RPM Ne of the internal combustion engine 1 is calculated on the basis of the signal coming from the rotation angle sensor 20 in the distributor 20. Next, the routine advances to step S102, at which it is determined whether or not the cooling water temperature THW based on the signal coming from the water temperature sensor 31 is over a predetermined temperature, 0° C. This determination condition requires no determination processing because the fuel injection rate (amount) is set in advance to establish a rich side air/fuel ratio so as to maintain the startability at a low temperature side below 0° C. so that a predetermined drivability is achieved even from the heavy fuel. With a failure in rotation at an overrich air/fuel ratio, on the other hand, there arises a disadvantage that the failure leads to a determination of the heavy fuel.

Figure 4:
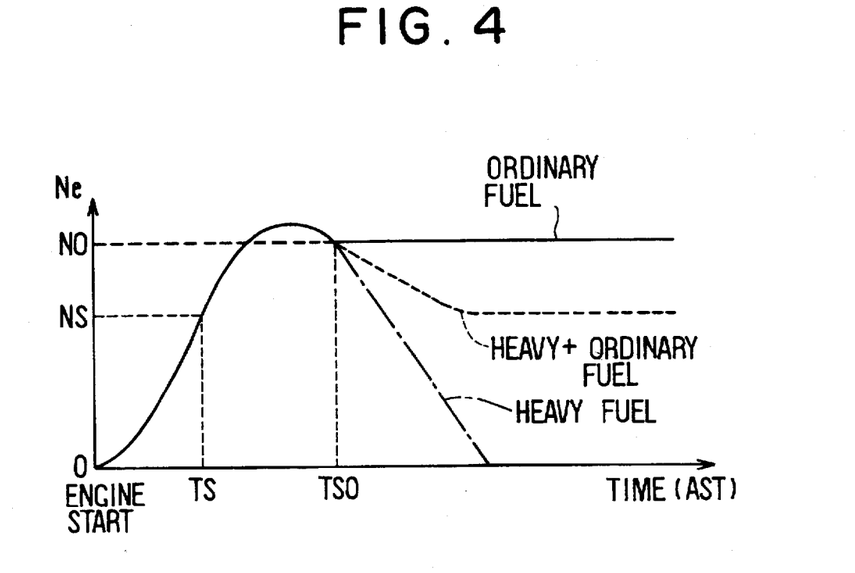
FIG. 4 is a characteristic diagram plotting an engine RPM against an elapsed time after the start of the internal combustion engine when the fuel to be used in the fuel property detecting routines of FIGS. 2 and 3 is exemplified by an ordinary fuel, a mixture of heavy and ordinary fuels, and a heavy fuel.

If the determination condition for step S102 is satisfied (YES) to indicate that the cooling water temperature is over 0° C., the routine advances to step S103, at which it is determined whether or not a after-start time AST longer than TS has elapsed from the start of the internal combustion engine 1. This time TS (FIG. 4) is set to a value from the time the IG 33 is turned on to energize the not-shown starter to the time the internal combustion engine 1 will attain a complete explosion or combustion of fuel in the cylinder (engine RPM NS in FIG. 4 is about 500 rpm). If the determination condition for step S103 is satisfied, the routine advances to step S104, at which it is determined whether or not the elapsed time AST after the start of the internal combustion engine 1 is below TE which correspond to the time in which the engine will have been warmed up sufficiently. The determination of volatility after the time TE is inappropriate, because the internal combustion engine 1 will have been already warmed up even for the heavy fuel at the lapse of the time TE after the engine start so that the combustion and accordingly the engine RPM Ne are stabilized.

If the determination condition for the step S104 is satisfied, the routine advances to step S105, at which it is determined whether or not the engine RPM Ne of the internal combustion engine 1 has exceeded a set engine RPM (or target RPM) NO and become lower than the set engine RPM NO which is about 1,200 rpm. If the determination condition for step S105 is satisfied, i.e., at the time TSO (FIG. 4), the routine advances to step S106, at which an execution flag is set to "1". If the determination condition for step S105 is not satisfied (NO), on the other hand, the routine advances to step S107, at which it is determined whether or not the execution flag is at 1. After the operation of step S106 or with the satisfaction of the determination condition for step S107, the routine advances to step S108, at which the engine RPM Ne currently calculated at step S101 is added or integrated to the previously integrated value NT(i−1) so that the sum is used as the integrated value NT(i) of the engine RPM at this time. Thus, the number of rotations of the engine 1 after the time TSO is integrated. Next, the routine advances to step S109, at which the set engine RPM NO is added to the integrated value NOT(i−1) of the preceding set engine RPM so that the sum is used as the integrated value NOT(i) of the set engine RPM at this time.

Figure 5:
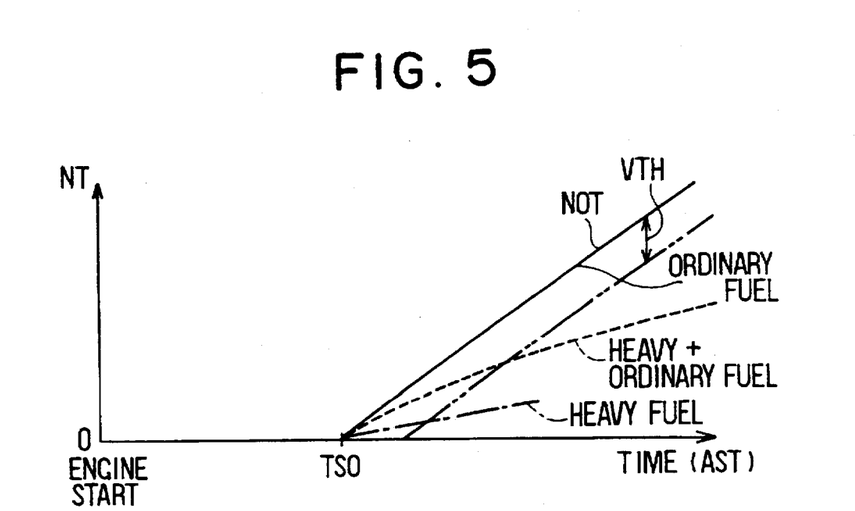
FIG. 5 is a characteristic diagram plotting an integrated value of the engine RPM against the elapsed time after the start of the internal combustion engine when the fuel to be used in the fuel property detecting routines of FIGS. 2 and 3 is exemplified by the ordinary fuel, the heavy-ordinary fuel mixture, and the heavy fuel.

Next, the routine advances to step S110, at which it is determined whether or not the deviation (NOT−NT) between the integrated value NOT(i) of the set engine RPM, as determined at step S109, and the integrated value NT(i) of the engine RPM, as determined at step S108, is larger than a deviation VTH which is made for the predetermined heavy fuel and about 200 rpm. As shown in FIG. 5, the engine RPM Ne of the internal combustion engine 1 is always in the vicinity of the set engine RPM NO for the ordinary fuel so that the integrated value NT of the engine RPM becomes equal to the integrated value NOT of the set engine RPM. For the heavy fuel or the mixture of the fuel and the heavy fuel, on the other hand, the integrated value NT of the engine RPM is smaller than that for the ordinary fuel. Thus, whether or not the fuel is an ordinary one can be determined by comparison with the deviation VTH or the offset value from the integrated vale NOT of the set engine RPM. The integrated value NOT of the set engine RPM is determined for each execution of the routine in the present embodiment, but the set engine RPM NO may be set to a constant relating to the time because it is known in advance.

If the determination condition for step S110 is satisfied to indicate that NOT−NO>VTH, the routine advances to step S111, at which it is determined that the fed fuel is heavy, and the present routine is ended. If the determination conditions for Step S102 to S104 or step S107 are not satisfied (NO), the routine skips to step So, at which the execution flag is set to "0", and the present routine is ended. If the determination condition is not satisfied, on the other hand, the present routine is ended without any operation.

In the routine, if step S111 determines the heavy fuel, the combustion of the internal combustion engine 1 may be stabilized, although not shown in the present embodiment, by enriching (increasing) the fuel amount feed from the injector 25 to the internal combustion engine 1 or by opening a not-shown ISC (Idle Speed Control) valve thereby to raise the engine rotation RPM.

Figure 2:
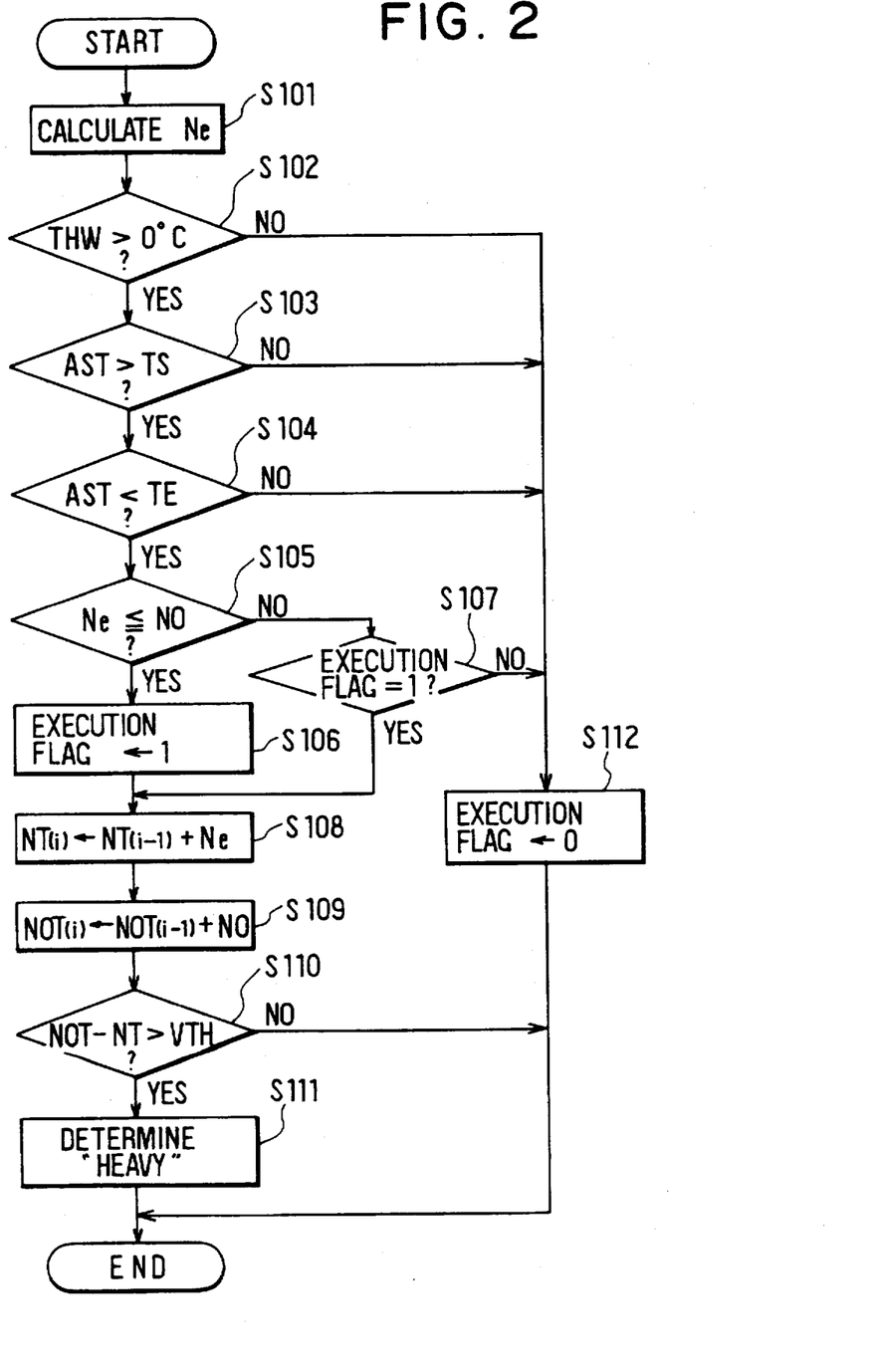
FIG. 2 is a flow chart showing a routine for detecting the fuel properties in a CPU of an ECU, as used in the fuel property detecting system for an internal combustion engine according to the first embodiment of the present invention.
Figure 3:
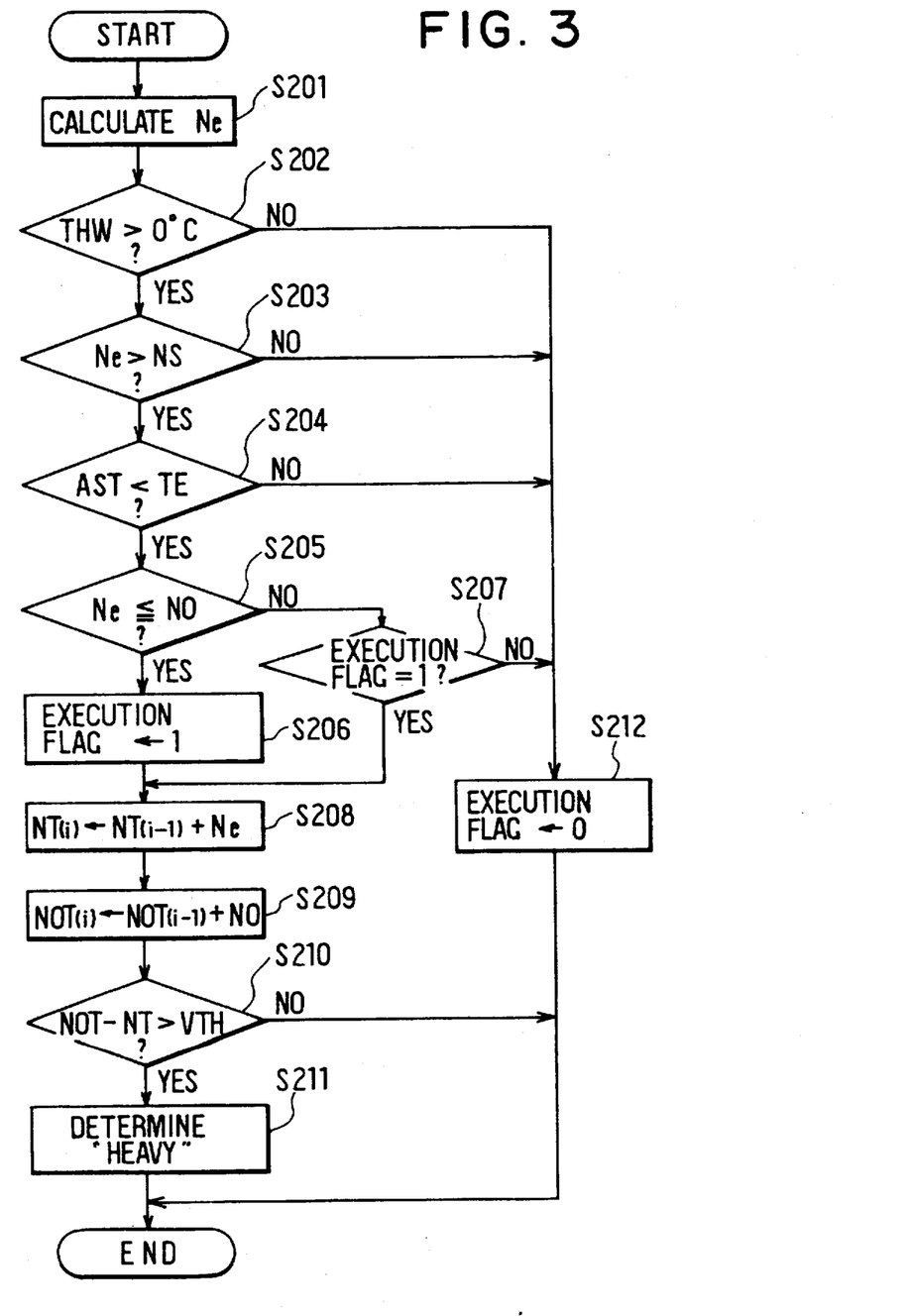
FIG. 3 is a flow chart showing a partially modified routine for detecting the fuel properties according to the first embodiment of the present invention.

The routine of FIG. 2 may be partly modified to the routine shown in FIG. 3. Steps So to So of FIG. 3 excepting step So correspond to steps S101 to So of FIG. 2 excepting step S103, respectively.

At step So of FIG. 3, it is determined whether or not the engine RPM Ne of the internal combustion engine 1 has ever exceeded a complete explosion RPM NS (corresponding to time TS in FIG. 4) even once after the start. Specifically, this complete explosion engine RPM NS is set to a value at which the IG is turned ON to rotate the not-shown starter so that the internal combustion engine 1 will reach its complete explosion state.

In the present embodiment, the engine RPM Ne during the elapsed time after the start AST is integrated, and the integrated value NT of the engine RPM is compared with the integrated value NOT of the set engine RPM for the ordinary fuel. If the integrated value NT of the engine RPM and the integrated value NOT of the set engine RPM are equal at this time, it is determined that the feed fuel of the internal combustion engine 1 for the ordinary fuel is volatile. As a result, the properties of the fuel, as fed to the internal combustion engine, are detected to indicate whether it is ordinary or heavy (containing the mixed fuel).

After the engine RPM Ne is stabilized, the deviation (NOT−NT) and the predetermined determination value VTH or the offset value are compared to determine the volatility of the fuel fed to the internal combustion engine 1. As a result, the reliability of the determination of the properties of the fuel fed to the internal combustion engine 1.

In the present embodiment, moreover, the determination value VTH may be changed in accordance with the temperature of the internal combustion engine 1. As the internal combustion engine 1 is more warmed up or high in temperature, there appears less difference of the engine RPM Ne, as depending upon the properties of the fuel fed to the internal combustion engine 1. As the internal combustion engine 1 is more warmed up, therefore, the determination value VTH is made smaller to make it easier to detect the properties of the fuel fed to the internal combustion engine 1, so that it is determined whether the fuel is the ordinary one or the other heavy one (including the mixed fuel).

In the present embodiment, still moreover, as the internal combustion engine 1 is more warmed up, there appears the less difference of the engine RPM Ne, as depending upon the properties of the fuel fed to the internal combustion engine 1. When the predetermined lapsed time range is passed from the starting point, the internal combustion engine 1 also comes into the warmed-up state so that the difference of the engine RPM Ne, as depending upon the properties of the feed fuel to the internal combustion engine 1, becomes less likely to appear. Thus, the determination is made before the internal combustion engine 1 is completely warmed up and within a predetermined lapsed time range after the starting point. As a result, it becomes easy to detect the properties of the fuel fed to the internal combustion engine 1, and it is determined whether the fuel is the ordinary one or the other heavy one (including the mixed fuel).

In the present embodiment, furthermore, the engine RPM Ne within the lapsed time after the start when it is detected by the water temperature sensor 31 that the cooling water temperature of the internal combustion engine 1 exceeds the predetermined temperature is integrated, and this integrated value NT of the engine RPM and the integrated value NOT of the set engine RPM for the ordinary fuel are compared to determine the volatility of the fed fuel. That is, when the cooling water temperature of the internal combustion engine 1 is lower than the predetermined level, the fuel is usually enriched (corrected to increase in amount) so that the determination of the fuel properties is not made. As a result, the properties of the fuel fed to the internal combustion engine are accurately detected so that the fuel is discriminated whether it is ordinary or heavy (including the mixed fuel).

<Embodiment 2>

Figure 6:
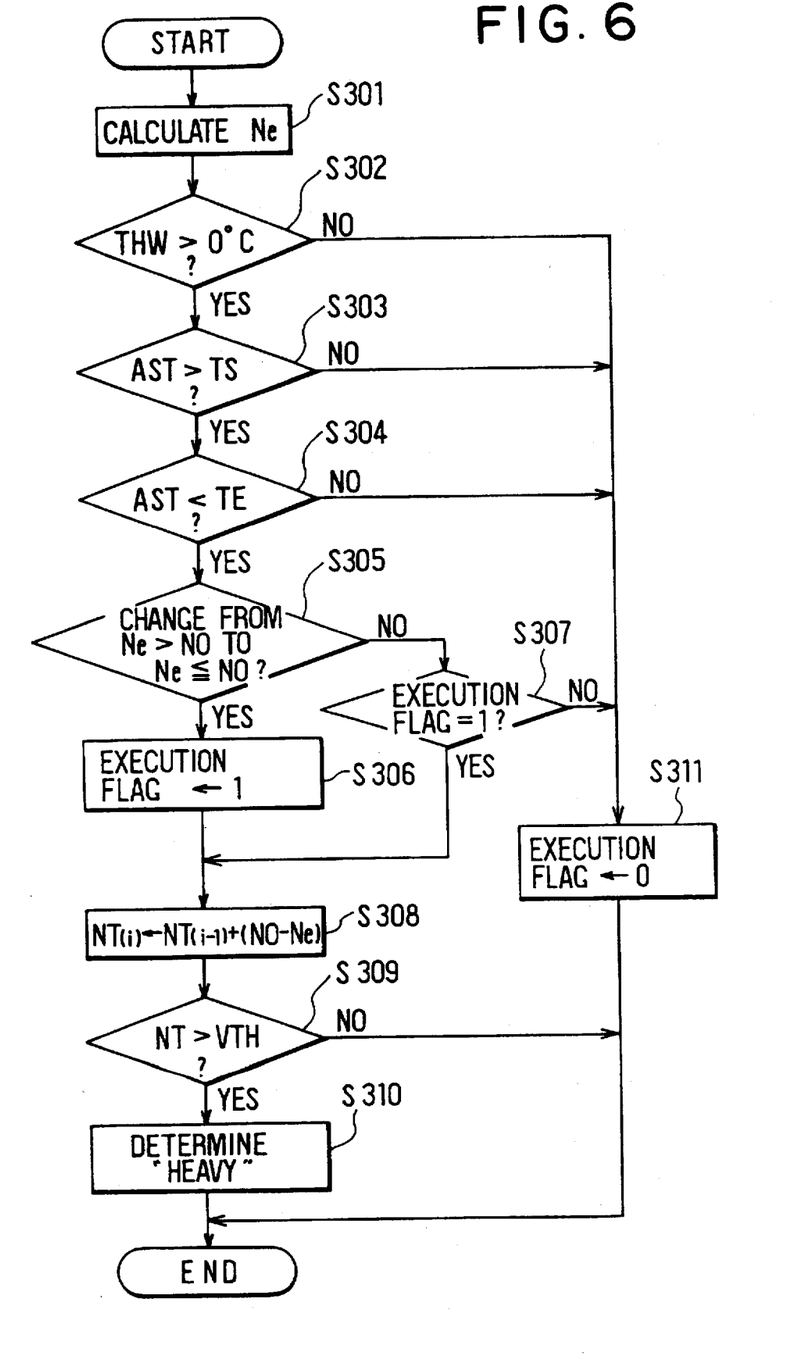
FIG. 6 is a flow chart showing a routine for detecting the fuel properties according to a second embodiment of the present invention.

According to the second embodiment shown in FIG. 6, at first step So the engine RPM Ne of the internal combustion engine 1 is calculated on the basis of the signal coming from the rotation angle sensor 20a in the distributor 20. Next, the routine advances to step So, at which it is determined whether or not the cooling water temperature THW based on the signal coming from the water temperature sensor 31 is over a predetermined temperature, 0° C.

If the determination condition for step So is satisfied to indicate that the cooling water temperature is above 0° C., the routine advances to step S303, at which it is determined whether or not a time longer than TS has elapsed from the start of the internal combustion engine 1. If the determination condition for step S303 is satisfied, the routine advances to step S304, at which it is determined whether or not the elapsed time AST after the start of the internal combustion engine 1 is below TE.

If the determination condition for the step S304 is satisfied, the routine advances to step S305, at which it is determined, whether or not the engine RPM Ne of the internal combustion engine 1 has exceeded a set engine RPM (or target RPM) NO and then became lower than the set engine RPM NO as shown in FIG. 4. If the determination condition for step S305 is satisfied, the routine advances to step S306, at which an execution flag is set to "1". If the determination condition for step S305 is not satisfied, on the other hand, the routine advances to step S307, at which it is determined whether or not the execution flag is at 1. After the operation of step S306 or with the satisfaction of the determination condition for step S307, the routine advances to step S308, at which deviation (NO–Ne) between the engine RPM Ne and the set engine RPM NO is added to the precedingly integrated value NT(i–1) of the engine RPM so that the sum is used as the integrated value NT(i) of the engine RPM at this time.

Next, the routine advances to step S309, at which it is determined whether or not the integrated value NT of the deviation of the engine RPM, as determined at step S308, is over the threshold value VTH of the integrated value of the deviation of the engine RPM, as occurs for the preset heavy fuel. If the determination condition for step S309 is satisfied, the routine advances to step S310, at which it is determined that the fed fuel is heavy, and the present routine is ended. If the determination conditions for Step S S302 to S304 or step S307 are not satisfied, on the other hand, the routine advances to step S311, at which the execution flag is set to "0", and the present routine is ended. If the determination condition for step S309 is not satisfied, on the other hand, the present routine is ended without any operation.

If step S310 determines the heavy fuel, the combustion of the internal combustion engine 1 may be stabilized, although not shown in the present embodiment, by enriching the fuel, i.e., increasing the amount of fuel fed from the injector 25 to the internal combustion engine 1 or by enlarging the opening of the ISC valve (not shown).

Thus, in the present embodiment, the determination is made on the basis of the result of comparing the integrated value NT of the deviation between the engine RPM Ne and the set engine RPM NO with the predetermined determination value VTH, at every constant times or at every constant angles after the engine RPM Ne becomes lower than the preset engine RPM NO.

As a result, after the engine RPM Ne is stabilized, the volatility of the fuel fed to the internal combustion engine 1 is determined by comparing the integrated value NT of the deviation and the predetermined determination value VTH as the offset value. Thus, the determination on the properties of the fuel fed to the internal combustion engine 1 is improved.

Figure 7:
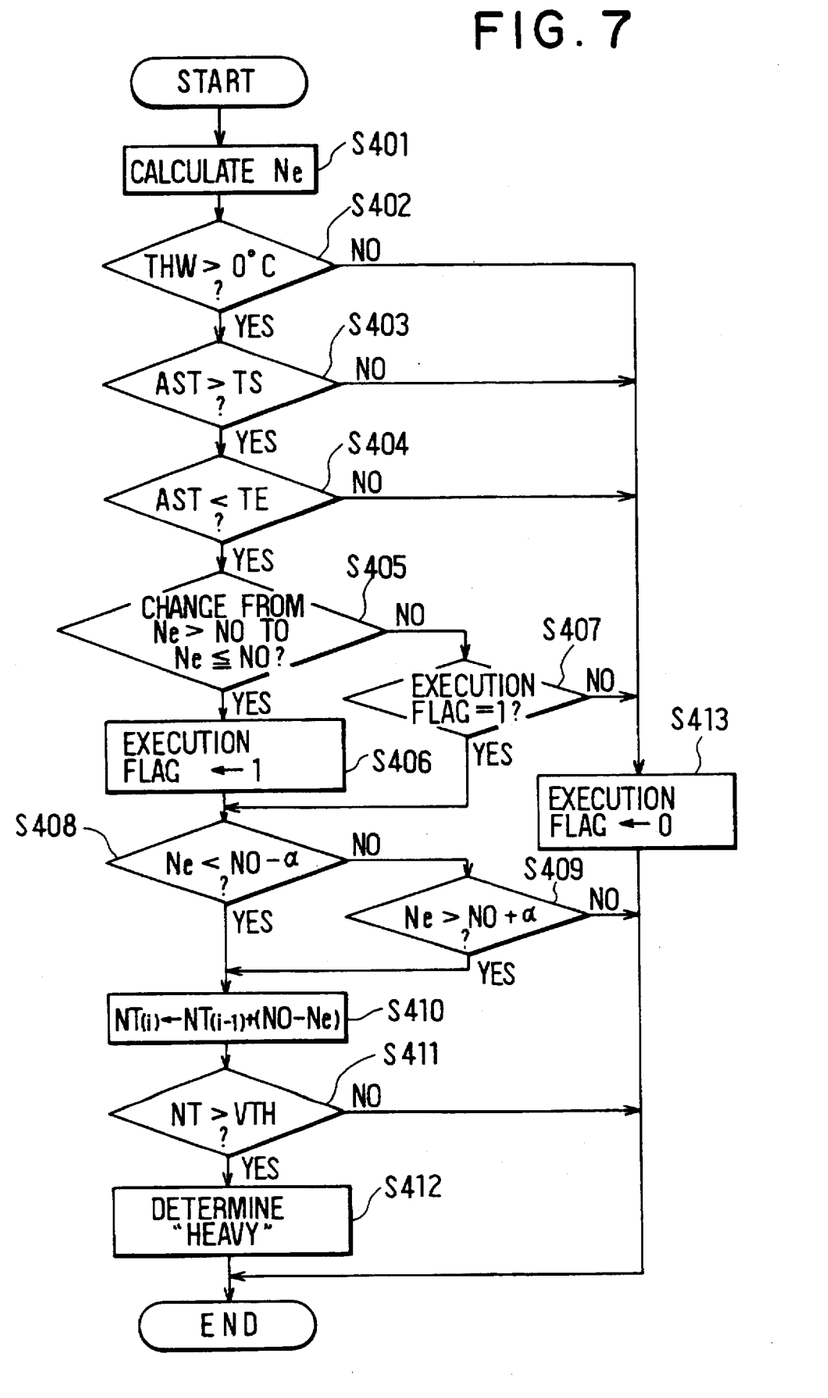
FIG. 7 is a flow chart showing a partially modified routine for detecting the fuel properties of FIG. 6.

The second embodiment may be partly modified to the routine shown in FIG. 7, in which steps S401 to S407 are executed similarly to steps S301 to S307 of FIG. 6. Then, the routine advances to step S408, at which it is determined whether or not the engine RPM Ne is below the difference which is calculated by subtracting a predetermined value $\alpha$ from the preset engine RPM NO. If the determination condition for step S408 is not satisfied, the routine advances to step S409, at which it is determined whether or not the engine RPM Ne is over the sum of the preset engine RPM NO and the predetermined value $\alpha$. If the determination condition for the step S409 is not satisfied, the present routine is ended without any operation. If the determination conditions for steps S408 and S409, moreover, operations similar to those of steps S308 to S311 of FIG. 6 are executed at steps S410 to S413.

In short, in the fuel property detecting routine of FIG. 7, the set engine RPM NO is given a deviation width of the predetermined value $\alpha$ to eliminate the fluctuation for the set engine RPM NO of the engine RPM Ne, and the only the deviation (NO–Ne) between the engine RPM Ne when the deviation width is exceeded and the set engine RPM NO is integrated. This enhances the reliability of the integrated value NT of the deviation thereby to improve the reliability of the determination on the properties of the fuel fed to the internal combustion engine.

<Embodiment 3>

Figure 8:
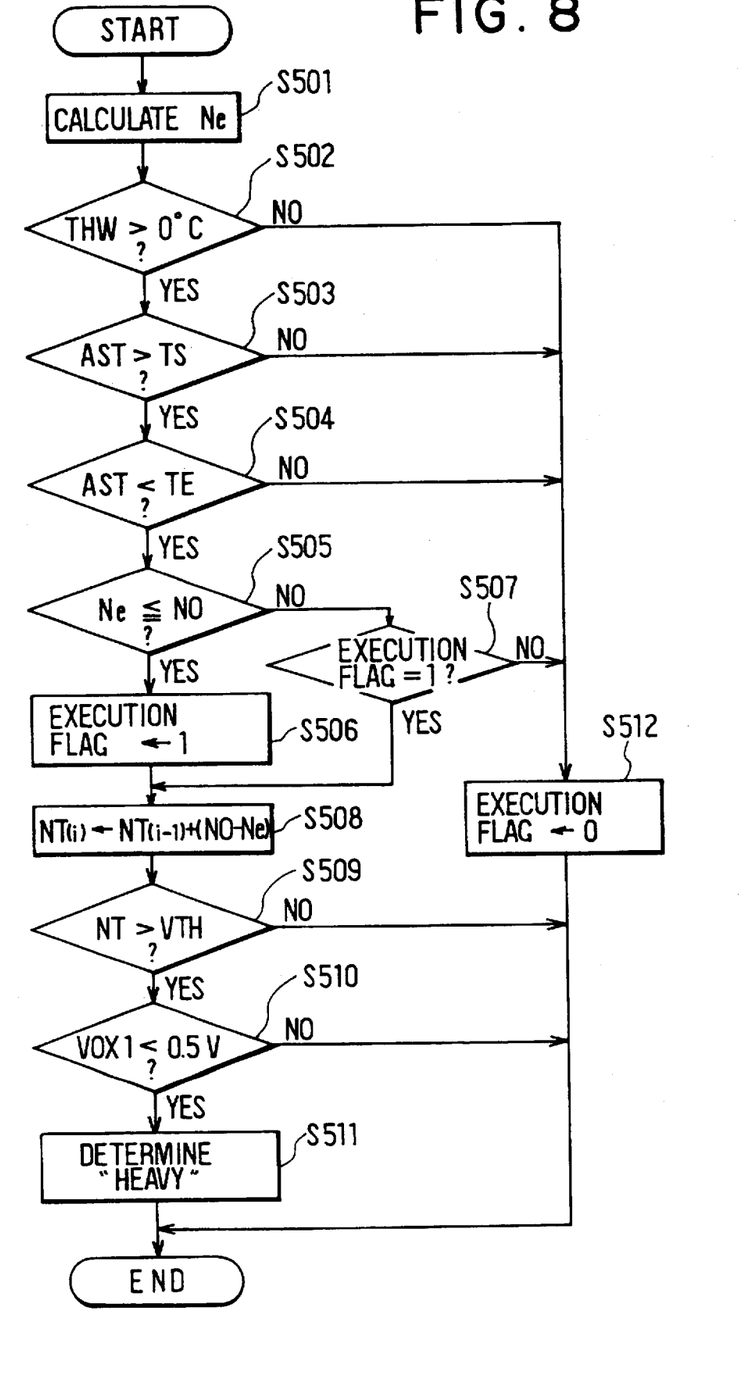
FIG. 8 is a flow chart showing a routine for detecting the fuel properties according to a third embodiment of the present invention.

In the third embodiment shown in FIG. 8 which is similar to the embodiment of FIG. 6, steps S501 to S512 excepting step S510 correspond to steps S301 to S311 of FIG. 6, respectively. At step S510 of FIG. 8, it is determined whether or not an air/fuel ratio signal VOX1 coming from the oxygen sensor 32 is at a lean side less 0.5 V. If the determination condition for step S510 is satisfied, i.e., the air/fuel ratio is leaner than the stoichiometric ratio (corresponding to 0.5 V, the routine advances to step S511, at which it is determined that the fed fuel is heavy, and the present routine is ended. If the determination condition for step S510 is not satisfied and if the air/fuel ratio is at the rich side, on the other hand, the determination is made on the heavy fuel so that the correction is made to increase the fuel. Then, the internal combustion engine 1 is made liable to stall by the over-richness, and the present routine is ended without any operation.

Thus, in the present embodiment, the determination of the volatility of the fed fuel is inhibited if the air/fuel ratio of the exhaust gas from the internal combustion engine 1 is at the rich side. As a result, the fuel fed is not corrected to increase if the air/fuel ratio of the exhaust gas from the internal combustion engine 1 is at the rich side. As a result, the engine stall of the internal combustion engine 1 due to the excess feed of the fuel can be prevented when the fuel fed to the internal combustion engine 1 is the heavy one.

<Embodiment 4>

Figure 9:
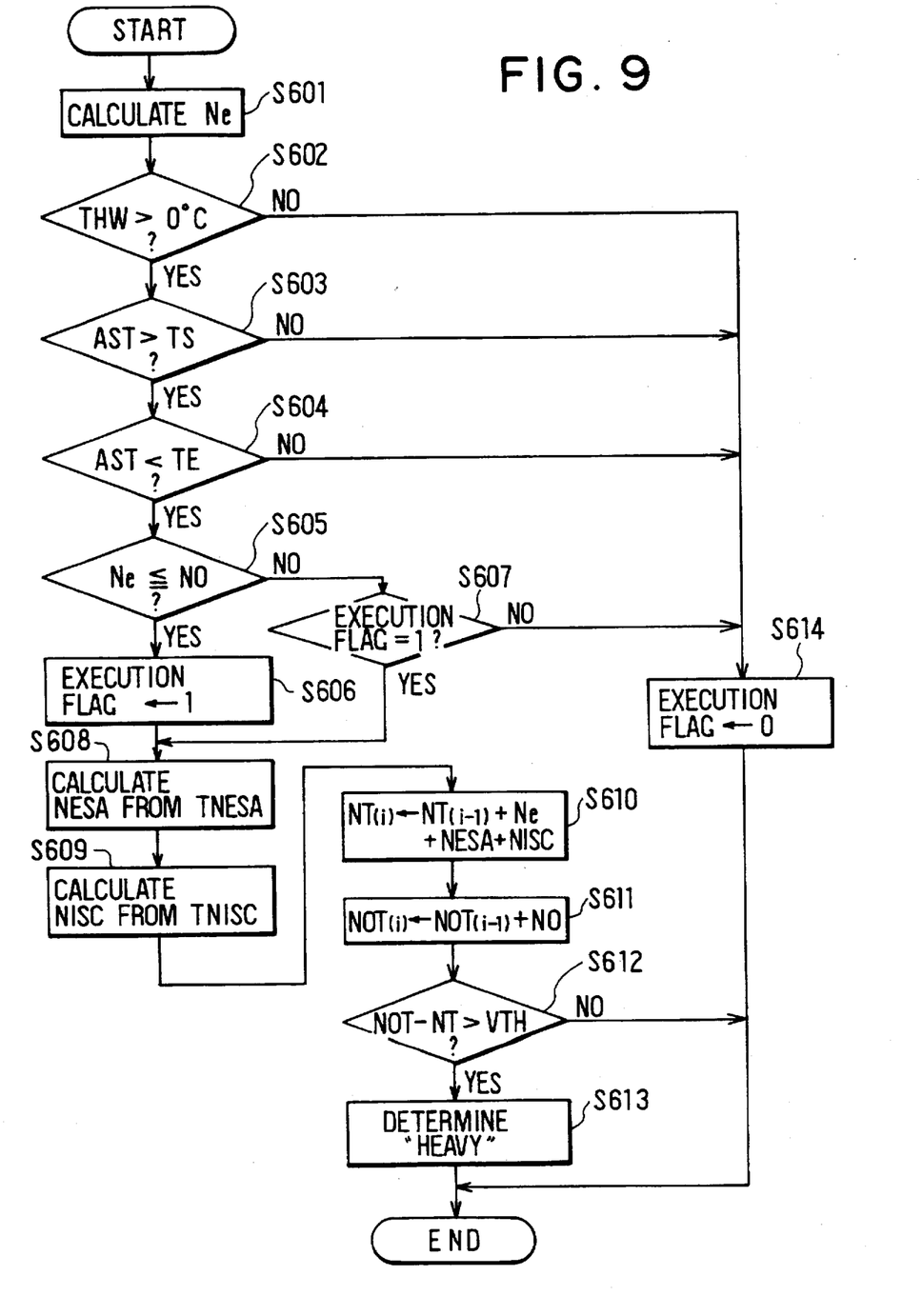
FIG. 9 is a flow chart showing a routine for detecting the fuel properties according to a fourth embodiment of the present invention.

In the fourth embodiment shown in FIG. 9 which is similar to the first embodiment shown in FIG. 2, steps S601 to S614 excepting steps S608 to S610 correspond to steps S101 to S112 of FIG. 2, respectively.

Figure 10:
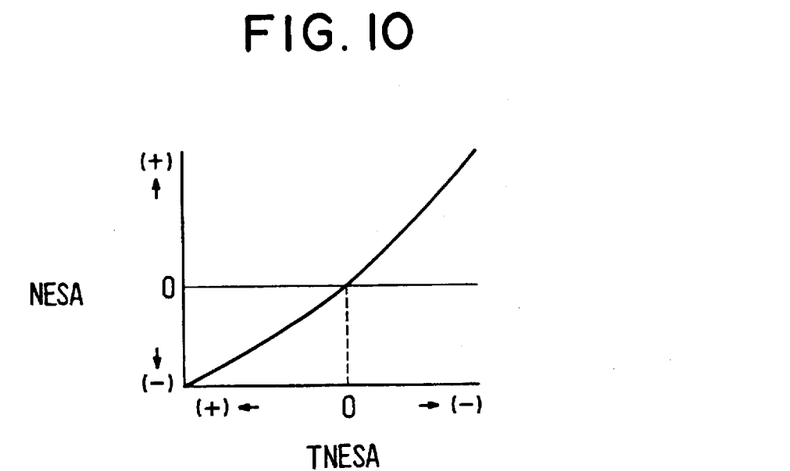
FIG. 10 is a characteristic diagram plotting a corrected engine RPM against the difference of (the demanded ignition timing–the actual ignition timing), as used in the fuel property detecting routine of FIG. 9.
Figure 11:
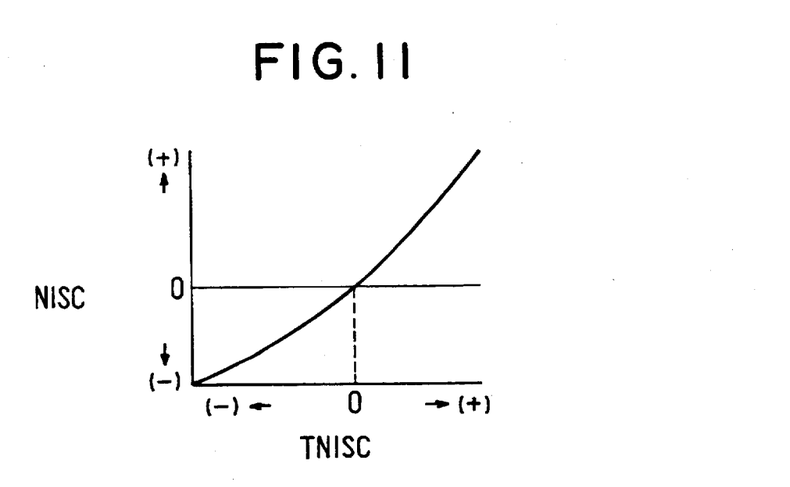
FIG. 11 is a characteristic diagram plotting a corrected engine RPM against the difference of (the demanded ISC opening–the actual ISC opening), as used in the fuel property detecting routine of FIG. 9.

At step S608, as shown in FIG. 10, a correction value NESA for the engine RPM is calculated on the basis of the ignition timing difference TNESA (the desired ignition timing–the actual ignition timing). Next, the routine advances to step S609, at which a correction value NISC for the engine RPM is calculated on the basis of the ISC opening difference TNISC (the desired ISC opening–the actual ISC opening) as shown in FIG. 11. Next, the routine advances to step S610, at which the actual engine RPM Ne, the correction value NESA calculated at step S608 and the correction value NISC calculated at step S609 are added to the preceding integrated value NT(i–1) of the engine RPM, to determine the integrated value NT(i) of the engine RPM at this time.

As a result, the properties of the fuel fed to the internal combustion engine 1 can be accurately determined by adding the ignition timing correction and the ISC opening correction due to the engine RPM behaviors.

Figure 12:
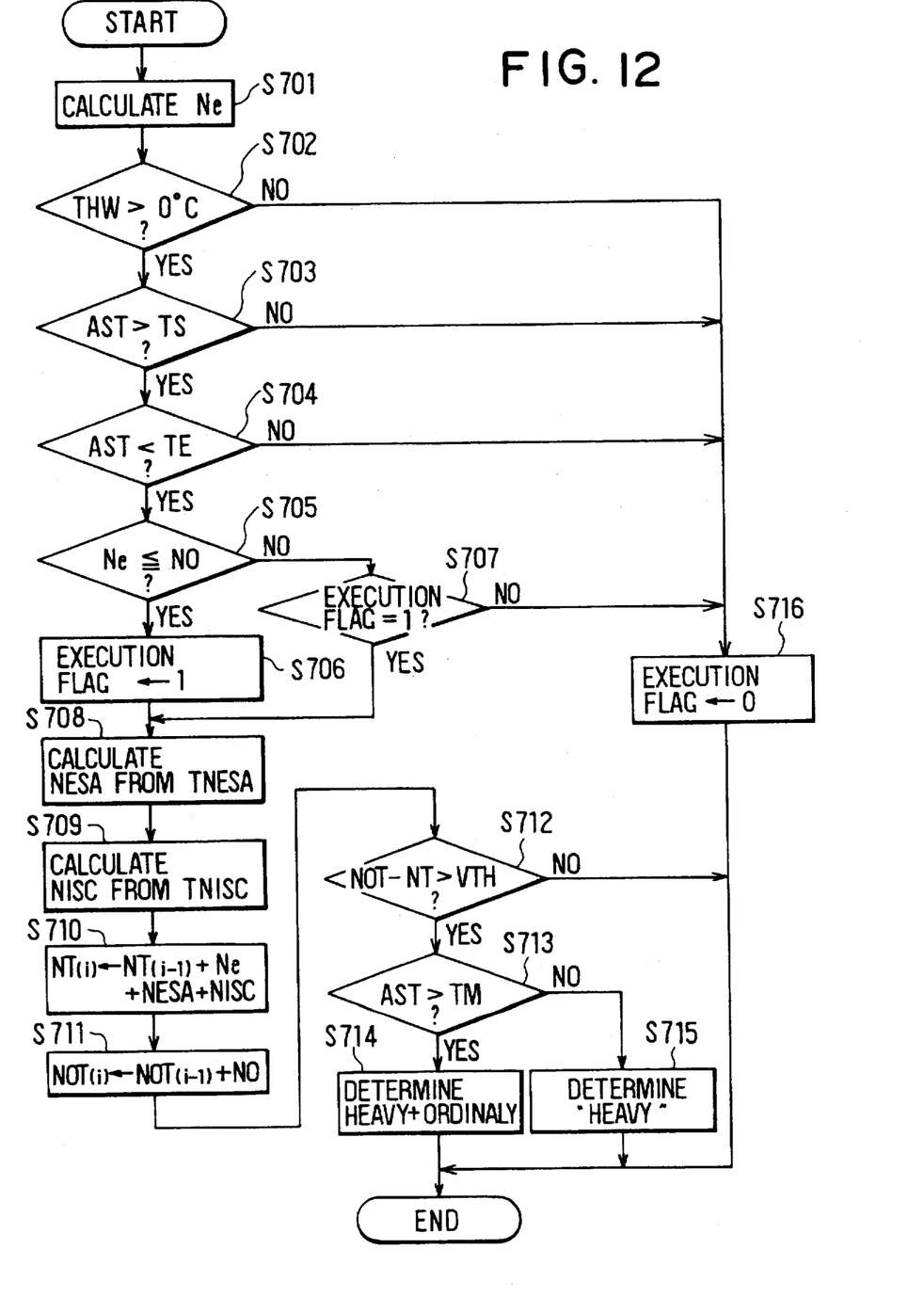
FIG. 12 is a flow chart showing a partially modified routine for detecting the fuel properties of FIG. 9.

The fourth embodiment may be modified as shown in FIG. 12, in which steps S701 to S716 excepting step S713 to S715 correspond to steps S601 to S614 of FIG. 9, respectively.

At step S713 it is determined whether or not there has elapsed from the start of the internal combustion engine 1 the time period TM which is set between more than the time TS from the start of the internal combustion engine 1 of step S703 and less than the time TE from the start of the internal combustion engine 1 of step S704. The time TM is set as the time period for determining the mixed fuel of an intermediate one (or the mixture of the heavy and ordinary fuels) between the ordinary fuel and the heavy fuel. If the determination condition for step S713 is satisfied, the time period more than the time TM has elapsed so that the deviation (NOT–NT) between the integrated value NOT of the set engine RPM the integrated value NT of the engine RPM exceeds the deviation VTH at step S712, and it is determined that the fuel fed to the internal combustion engine 1 is a mixed one. If the determination condition for step S713 is not satisfied, on the other hand, before the lapse of the time TM, the deviation (NOT–NT) between the integrated value NOT of the set engine RPM and the integrated value NT of the engine RPM exceeds the deviation VTH at step S712. Therefore, it is determined that the fuel fed to the internal combustion engine 1 is a heavy one, and the present routine is ended.

<Embodiment 5>

Figure 15:
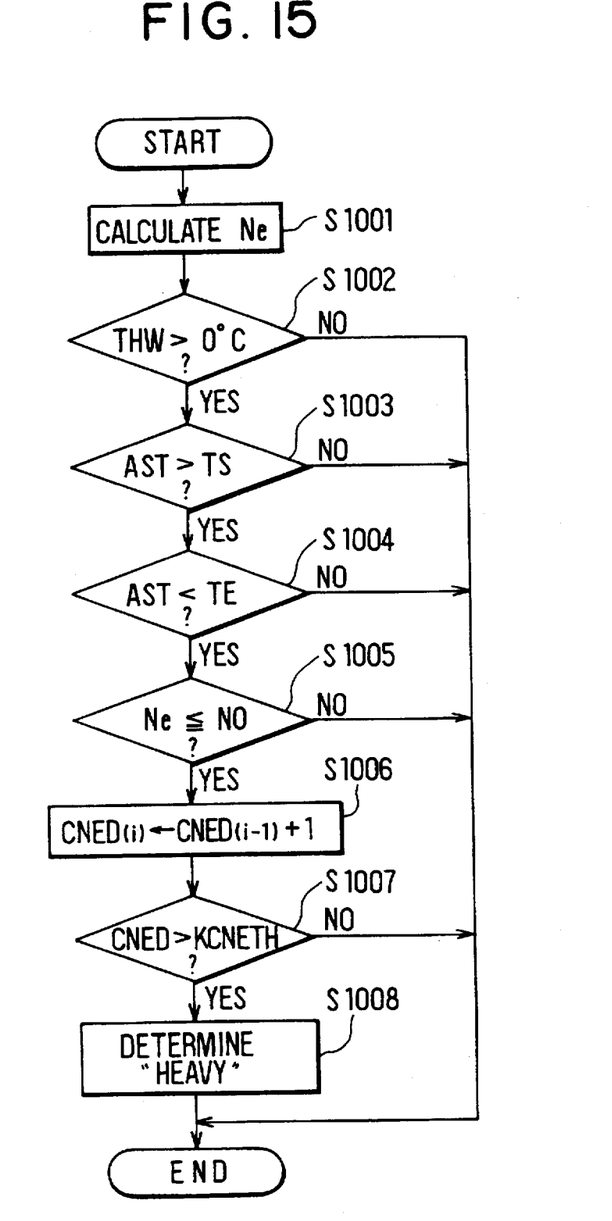
FIG. 15 is a flow chart showing a routine for detecting the fuel properties according to a fifth embodiment of the present invention.

In the fifth embodiment shown in FIG. 15 which is similar to the first embodiment shown in FIG. 2, steps S1001 to S1005 correspond to steps S101 to S105 of FIG. 2, respectively.

If it is determined at step S1005 that the engine RPM Ne is lower and higher than the preset engine RPM NO, steps S1006 follows and the process is ended, respectively. At step S1006, a count value CNED(i) counting the number of times step S1005 determines YES is incremented by one from the previous count value CNED(i–1). Then at step S1007, the count value CNED is compared with a predetermined threshold value KCNETH. If CNED is larger than KCNETH, step S1008 determined that the fuel is heavy one.

The fifth embodiment may be modified in such a manner that a timer measures the time lapse from the time when the engine RPM Ne becomes lower than the set RPM NO (YES determination at step S1005) and, if the measured time reaches a predetermined time, it is determined that the fuel is heavy one.

<Ignition Timing Delay Control

In the internal combustion engine control of recent years, for reducing the noxious content in the exhaust gas, the ignition timing is delayed angularly to effect the combustion at a stage near the exhaust stroke, and the exhaust gas at a high temperature is introduced into the catalyst converter 18 to promote the warming-up of the catalyst converter 18. The angular delay in the ignition timing makes the combustion of the internal combustion engine 1 unstable, and such an ignition delay may lead to engine stall if it is fed with the heavy fuel while being driven under the angular delay control. At the time of determination of the heavy fuel, therefore, the angular delay control of the ignition timing has to be inhibited to stabilize the combustion.

Therefore, a routine of the ignition timing control after the properties of the fuel fed to the internal combustion engine 1 have been determined in the foregoing embodiments will be described with reference to the flow chart of FIG. 13.

At step S801, it is determined whether or not the output signal from the IG 33 is ON so that the internal combustion engine 1 is being started. If the determination condition for step S801 is satisfied, the routine advances to step S802, at which it is determined in terms of the output signal from the water temperature sensor 31 whether or not the internal combustion engine 1 is cold. If the determination condition for step S802 is satisfied, the routine advances to step S803, at which it is determined whether or not the fed fuel is heavy, as described above. If the determination condition for step S803 is not satisfied, the routine advances to step S804, at which it is determined whether or not the lapsed time after the start of the internal combustion engine 1 has reached the start time (e.g., 3 seconds after the start) for executing the angular delay control. If it is determined at step S804 that the start time is not reached yet, this start time is awaited, and the routine advances to step S805. At step S805, it is determined whether or not the engine is idling. If the determination condition for step S805 is satisfied, the routine advances to step S806, at which the ignition delay control is actually executed on the basis of the preset target of the angular delay and the time for controlling the angular delay actually.

Figure 14:
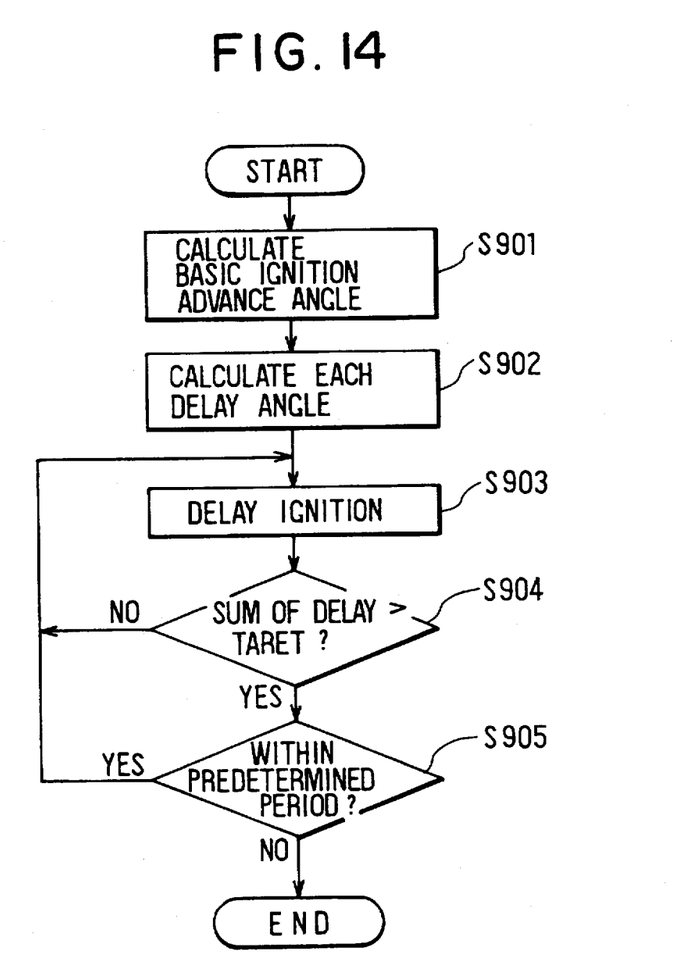
FIG. 14 is a flow chart showing a routine for controlling the ignition delay of FIG. 13.

The routine for this ignition delay control will be described in detail with reference to the flow chart of FIG. 14. At step S901, a basic ignition advance angle is calculated from the not-shown data map using the engine RPM Ne and the cooling water temperature THW of the internal combustion engine 1 as the parameters. Next, the routine advances to step S902, at which the delay angle for each arithmetic routine is calculated from the following formula by using the preset delay angle target and gradual changing delay angle time:

Delay Angle=Delay Angle Target×Calculation Period/Gradual Changing Delay Angle.

Next, the routine advances to step S903, at which the ignition timing is actually delayed with the value (or the corrected angular delay) which is determined by subtracting one angular delay for each arithmetic period from either the basic angular advance, as calculated at step S901, or the angular advance calculated at the previous time. Next, the routine advances to step S904, at which it is determined whether or not the sum of the subtracted angular delay has reached the angular delay target. If the determination condition for step S904 is satisfied, the routine advances to step S905, at which it is determined whether or not the execution of the angular delay control is within a predetermined period (e.g., 20 seconds from the start). If the determination condition for step S905 is satisfied or if the determination condition for step S904 is not satisfied, the routine returns to step S903, at which the angular delay control is continued. If the determination condition for step S905 is not satisfied and if the predetermined period is elapsed, the present routine is ended. Thus, the actual angular delay control of the ignition timing, as based upon the set angular delay, is executed by the aforementioned operations of Step S S901 to S905.

Figure 13:
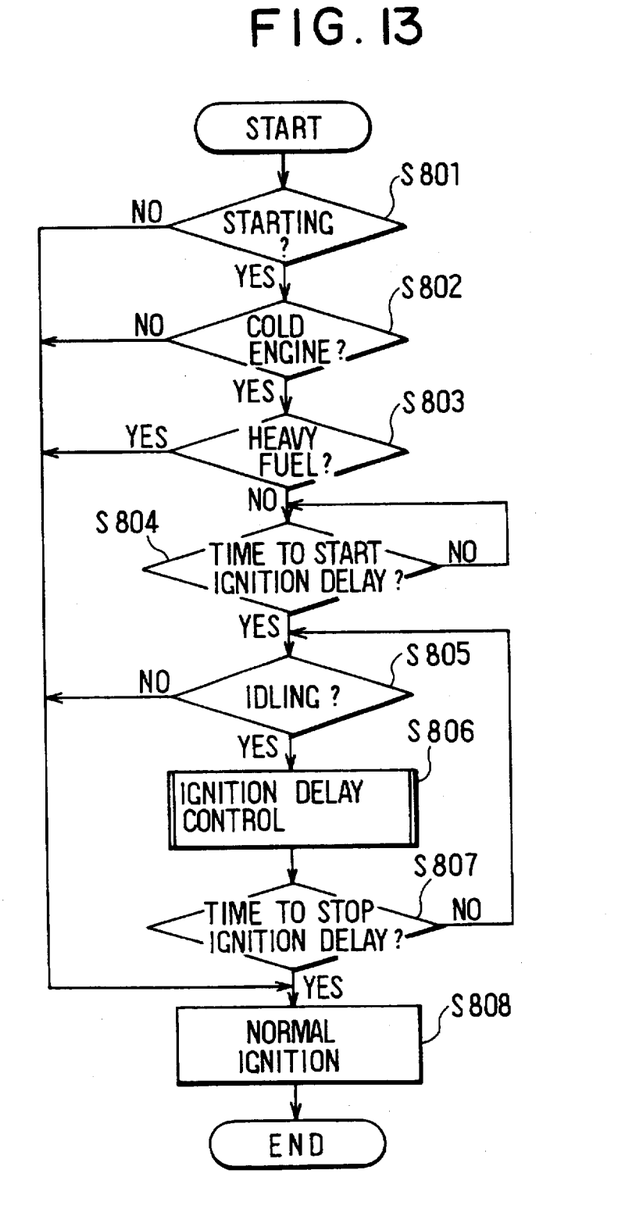
FIG. 13 is a flow chart showing a routine for controlling the ignition timing after the fuel property, as detected by the fuel property detecting system for an internal combustion engine according to the first to fourth embodiments of the present invention.

Next, the routine returns to step S807 of FIG. 13, at which it is determined whether or not the elapsed time after the start of ignition delay control is within the time range for which the angular delay control is executed, that is, whether or not the ignition delay control period (e.g., 18 seconds from the start) has been reached. If the determination condition for step S807 is not satisfied, the routine returns to step S805 so that the operations of steps S805 to S807 are repeatedly executed. On the other hand, if the determination conditions for steps S801 and S802 are not satisfied, if the determination condition for step S803 is satisfied, if the determination condition for step S805 is not satisfied and if the determination condition for step S807 is satisfied, the routine advances to step S808, at which the normal control of the ignition advance is executed in place of the ignition delay control, and the present routine is ended.

Thus, the angular delay of the ignition timing of the internal combustion engine 1 is inhibited if the volatility of the fuel fed to the internal combustion engine 1 poorer than that of the ordinary one.

That is, the angular delay of the ignition timing of the internal combustion engine 1 is inhibited if it is determined that the fuel fed to the internal combustion engine 1 is the heavy one. As a result, the engine RPM Ne of the internal combustion engine 1 can be prevented in advance from becoming unstable, thereby to prevent the engine stall.

It is to be noted that the present invention should not be limited to the disclosed embodiments but may be interpreted to cover other embodiments within the scope and spirit of the invention.

What is claimed is:

1. A fuel property detecting system for an internal combustion engine, comprising:

speed detecting means for detecting a rotation speed of an internal combustion engine;

speed integrating means for integrating the engine speed detected by said speed detecting means for a predetermined period of time after a start of said internal combustion engine; and volatility determining means for determining the volatility of fuel fed to said internal combustion engine, on the basis of an integrated value of said engine speed integrated by said speed integrating means in relation to a predetermined determination value.

2. A fuel property detecting system according to claim 1, wherein:

said volatility determining means determines the volatility by comparing, at every predetermined interval after the engine speed detected by said speed detecting means after the start of said internal combustion engine becomes lower than a predetermined engine speed, a difference between the integrated value of said engine speed and an integrated value of the predetermined engine speed with said predetermined determination value.

3. A fuel property detecting system according to claim 1, wherein:

said volatility determining means determines the volatility by comparing, at every predetermined interval after the engine speed detected by said speed detecting means after the start of said internal combustion engine becomes lower than a predetermined engine speed, an integrated value of a deviation between said engine speed and said predetermined engine speed with said predetermined determination value.

4. A fuel property detecting system according to claim 1, wherein:

the predetermined determination value is changed on the basis of a temperature of said internal combustion engine.

5. A fuel property detecting system according to claim 1, wherein:

said volatility determining means determines the volatility within a predetermined elapsed time from a starting point determined by a temperature of said internal combustion engine.

6. A fuel property detecting system according to claim 1, wherein:

said volatility determining means inhibits a determination of the volatility when an air/fuel ratio of mixture detected in an exhaust gas from said internal combustion engine is at a rich side.

7. A fuel property detecting system according to claim 1, wherein:

said volatility deciding means inhibits ignition angle delay control for said internal combustion engine if the volatility of the fuel is determined to be poorer than that of an ordinary fuel.

8. A fuel property detecting system according to claim 1, further comprising:

water temperature detecting means for detecting a cooling water temperature of said internal combustion engine, wherein said speed integrating means integrates said engine speed when the cooling water temperature detected by said water temperature detecting means is above a predetermined temperature.

9. A fuel property detecting method for an internal combustion engine, comprising the steps of:

determining a first time point when a complete combustion of fuel occurs in the engine after an engine starting operation;

determining a second time point when an engine rotation speed attains a predetermined speed after the first time point;

integrating the number of engine rotations after the second time point; and comparing an integration output value of the engine rotations with a predetermined value thereby to determine the property of fuel.

10. The fuel property detecting method according to claim 9, further comprising the step of:

limiting the comparing step to an engine warm-up period.

11. The fuel property detecting method according to claim 9, further comprising the steps of:

detecting a temperature of the engine; and correcting at least one of the integration output value and the predetermined value in accordance with the detected temperature.

12. The fuel property detecting method according to claim 9, further comprising the steps of:

detecting an air/fuel ratio of mixture from an exhaust gas of the engine; and inhibiting the comparing step when the detected air/fuel ratio is in a fuel rich side.

* * * * *